(12) United States Patent
Pimplaskar (10) Patent No.: US 9,295,675 B2
(45) Date of Patent: *Mar. 29, 2016

(54) TESTOSTERONE GEL COMPOSITIONS AND RELATED METHODS

(71) Applicant: Upsher-Smith Laboratories, Inc., Maple Grove, MN (US)

(72) Inventor: Harish K. Pimplaskar, Charlotte, NC (US)

(73) Assignee: Upsher-Smith Laboratories, Inc., Maple Grove, MN (US)

(*) Notice: Subject to any disclaimer, the term of this patent is extended or adjusted under 35 U.S.C. 154(b) by 95 days.

This patent is subject to a terminal disclaimer.

(21) Appl. No.: 14/307,085

(22) Filed: Jun. 17, 2014

(65) Prior Publication Data

US 2015/0164913 A1 Jun. 18, 2015

Related U.S. Application Data

(63) Continuation of application No. 14/177,765, filed on Feb. 11, 2014, now Pat. No. 8,785,426.

(60) Provisional application No. 61/915,742, filed on Dec. 13, 2013.

(51) Int. Cl.
| | |
|---|---|
| *A61K 31/568* | (2006.01) |
| *A61K 47/32* | (2006.01) |
| *A61K 31/56* | (2006.01) |
| *A61K 9/00* | (2006.01) |

(Continued)

(52) U.S. Cl.
CPC ............. *A61K 31/568* (2013.01); *A61K 9/0014* (2013.01); *A61K 9/06* (2013.01); *A61K 31/56* (2013.01); *A61K 47/10* (2013.01); *A61K 47/14* (2013.01); *A61K 47/22* (2013.01); *A61K 47/32* (2013.01)

(58) Field of Classification Search
CPC ... A61K 31/565; A61K 31/57; A61K 31/568; A61K 9/0014; A61K 47/32; A61K 47/22
See application file for complete search history.

(56) References Cited

U.S. PATENT DOCUMENTS

| | | | |
|---|---|---|---|
| 4,863,970 | A | 9/1989 | Patel et al. |
| 5,023,252 | A | 6/1991 | Hseih |

(Continued)

FOREIGN PATENT DOCUMENTS

| | | |
|---|---|---|
| EP | 0 644 746 | 9/1999 |
| EP | 1 063 942 | 6/2004 |

(Continued)

OTHER PUBLICATIONS

Franz, Thomas J. "Percutaneous Absorption: On the Relevance of In Vitro Data," The Journal of Investigative Dermatology, vol. 64, No. 3: pp. 190-195 (1975).

(Continued)

*Primary Examiner* — Savitha Rao
*Assistant Examiner* — Angela Brown-Pettigrew
(74) *Attorney, Agent, or Firm* — Kagan Binder, PLLC (57) ABSTRACT

Described are gel compositions containing active pharmaceutical ingredient such as testosterone, solvent, and thickener, the gel compositions being useful for transdermal administration of the active ingredient to a patient, and related methods. Certain embodiments of the gel composition specifically exclude Hsieh enhancer.

20 Claims, 2 Drawing Sheets

(51) Int. Cl.
*A61K 9/06* (2006.01)
*A61K 47/10* (2006.01)
*A61K 47/14* (2006.01)
*A61K 47/22* (2006.01)

(56) References Cited

U.S. PATENT DOCUMENTS

| | | |
|---|---|---|
| 5,152,997 A | 10/1992 | Ebert et al. |
| 5,332,577 A | 7/1994 | Gertner et al. |
| 5,731,303 A | 3/1998 | Hsieh |
| 5,760,096 A | 6/1998 | Thornfeldt et al. |
| 5,885,565 A | 3/1999 | Elias et al. |
| 5,908,619 A | 6/1999 | Scholz |
| 6,019,997 A | 2/2000 | Scholz et al. |
| 6,267,984 B1 | 7/2001 | Beste et al. |
| 6,319,913 B1 | 11/2001 | Mak et al. |
| 6,503,894 B1 | 1/2003 | Dudley et al. |
| 6,579,865 B2 | 6/2003 | Mak et al. |
| 7,320,968 B2 | 1/2008 | Gyurik |
| 8,178,518 B2 | 5/2012 | Gyurik |
| 8,486,925 B2 | 7/2013 | Malladi et al. |
| 2002/0058650 A1 | 5/2002 | Mak et al. |
| 2002/0064547 A1 | 5/2002 | Chern et al. |
| 2003/0096012 A1 | 5/2003 | Besse et al. |
| 2003/0124191 A1 | 7/2003 | Besse et al. |
| 2003/0175329 A1 | 9/2003 | Azarnoff et al. |
| 2004/0146557 A1 | 7/2004 | Chern et al. |
| 2004/0175416 A1 | 9/2004 | Taravella et al. |
| 2004/0176476 A1 | 9/2004 | Gyurik |
| 2004/0198706 A1 | 10/2004 | Carrara et al. |
| 2005/0018272 A1 | 1/2005 | Kimura |
| 2005/0042173 A1 | 2/2005 | Besse et al. |
| 2005/0113353 A1 | 5/2005 | Dudley et al. |
| 2005/0192260 A1 | 9/2005 | Gyurik |
| 2007/0237822 A1 | 10/2007 | Malladi |
| 2011/0201586 A1 | 8/2011 | Dudley et al. |
| 2011/0245215 A1 | 10/2011 | Carrara et al. |
| 2013/0224268 A1 | 8/2013 | Alam et al. |
| 2013/0281416 A1 | 10/2013 | Gyurik |
| 2013/0295166 A1 | 11/2013 | Grenier et al. |

FOREIGN PATENT DOCUMENTS

| | | |
|---|---|---|
| EP | 1 484 033 | 12/2004 |
| WO | WO 93/25168 | 12/1993 |
| WO | WO 99/47073 | 9/1999 |
| WO | WO 02/17926 | 3/2002 |
| WO | WO 02/17927 | 3/2002 |
| WO | WO 03/000158 | 1/2003 |
| WO | WO 2004000263 | 12/2003 |
| WO | WO 2004/080413 | 9/2004 |
| WO | WO 2005/007100 | 1/2005 |
| WO | WO 2005000241 | 1/2005 |

OTHER PUBLICATIONS

Auxilium Pharmaceuticals, Inc., DPT Laboratories, Ltd., Testim Prescribing Information Medication Guide, pp. 1-25, revised Aug. 2013.
*Auxilium Pharmaceuticals, Inc. and FCB, LLC,* v. *Upsher-Smith Laboratories, Inc.,* "Civil Docket" U.S. District Court, Delaware, Case 1:13-cv-00148-SLR, pp. 1-18, printed Jan. 15, 2014.
*Auxilium Pharmaceuticals, Inc. and FCB, LLC,* v. *Upsher-Smith Laboratories, Inc.,* "Complaint for Patent Infringement (attachments Civil Cover Sheet and Exhibits A-J)" U.S. District Court, Delaware, Case 1:13-cv-00148-SLR, Doc. 1, pp. 1-25, Jan. 28, 2013.
*Auxilium Pharmaceuticals, Inc. and FCB, LLC,* v. *Upsher-Smith Laboratories, Inc.,* "Defendant Upsher-Smith Laboratories, Inc.'s Answer, Affirmative Defenses, and Counterclaims " U.S. District Court, Delaware, Case 1:13-cv-00148-SLR, Doc. 7, pp. 1-35, Jan. 30, 2013.
*Auxilium Pharmaceuticals, Inc. and FBC, LLC,* v. *Upsher-Smith Laboratories, Inc.,* "Memorandum Opinion" U.S. District Court, Delaware, Case 1:13-cv-00148-SLR, Doc. 120, pp. 1-15, Dec. 4, 2013.
*Auxilium Pharmaceuticals, Inc. and FCB, LLC,* v. *Upsher-Smith Laboratories, Inc.,* "Order" U.S. District Court, Delaware, Case 1:13-cv-00148-SLR, Doc. 121, p. 1, Dec. 4, 2013.
Gauthier, Eric. "Les Dioxolanes : Une Nouvelle Classe De Promoteur D'Absorption Percutanee," Doctorat: Pharmacologie Experimental et Clinique, Thèse de doctorat Pharmacie Paris 11, Chatenay (Jun. 30, 2000).
Steidle, C. et al. "AA2500 Testosterone Gel Normalizes Androgen Levels in Aging Males with Improvements in Body Composition and Sexual Functions," Journal of Clinical Endocrinology & Metabolism, 88(6): 2673-2681 (2003).
Guay, Andre T. "Absorption of Testosterone Gel 1% (Testim) from Three Different Application Sites," Journal of Sexual Medicine, 6:2601-2610, (2009).
*Auxilium Pharmaceuticals, Inc. and CPEX Pharmaceuticals, Inc.,* v. *Upsher-Smith Laboratories, Inc.,* Videotaped Deposition of: Harish K. Pirnplaskar, pp. 1-254, Nov. 4, 2009.

TESTOSTERONE GEL COMPOSITIONS AND RELATED METHODS

PRIORITY CLAIM

The present non provisional patent Application is a continuation of United States Application having Ser. No. 14/177,765, filed Feb. 11, 2014, and claims benefit under 35 USC §119(e) from United States Provisional Patent Application having Ser. No. 61/915,742, filed Dec. 13, 2013, entitled "TESTOSTERONE GEL COMPOSITIONS AND RELATED METHODS," the entirety of said patent applications are incorporated herein by reference in their entireties.

FIELD OF THE INVENTION

The invention relates to gel compositions containing active pharmaceutical ingredient such as testosterone, solvent, and gel-forming polymer (a.k.a. thickener), useful for transdermal administration of the active ingredient to a patient, and related methods.

BACKGROUND

Male hypogonadism is a common hormone deficiency in men that involves decreased functional activity of the gonads. Male hypogonadism results from a variety of conditions in which testosterone concentration is diminished below the normal range. The hypogonadic condition is sometimes linked with a number of physiological changes, such as diminished interest in sex, impotence, reduced lean body mass, decreased bone density, affected mood, and reduced energy levels.

In the United States, men of all ages are treated for hypogonadism use testosterone replacement therapy. Various methods of delivering testosterone have been considered and developed to provide suitable replacement therapies. Examples include intramuscular injections, pellet implants, transdermal patches, and hydroalcoholic testosterone gels. Commercial testosterone gels include AndroGel® testosterone gel from AbbVie, Inc., and Testim® testosterone gel from Auxilium, each of which is a one-percent testosterone gel that is administered by application of the gel to external skin surfaces whereafter testosterone in the gel passes through the akin. AndroGel® is also commercially available in a 1.62-percent testosterone gel product.

A testosterone gel is a medicinal formulation that can be applied externally to a patient's skin and deliver testosterone transdermally. These gels are designed to provide a combination of useful rheological, tactile, and functional (testosterone delivery) properties, preferably including desired pharmaceutical stability, and without undesirable odor, texture, or appearance. Rheological properties such as gel viscosity should allow a gel to be applied externally to skin and thereafter remain at that location of application for a period of uptake of the testosterone through the skin. Tactile properties relate to the feel and texture of the gel when touched and applied by a user, with preferred gels exhibiting a smooth feel. Good delivery properties (e.g., uptake) allow an effective amount of testosterone from the applied gel to be absorbed through skin during the time that the gel remains located at the skin surface.

Certain specific ingredients are included in commercial testosterone gel products to achieve desired properties of viscosity and uptake, such as enhancers, that is, a material which is capable of increasing the rate of passage of an androgen through a body membrane. For example, Testim® testosterone gel includes the chemically complex, cyclic oxacyclohexadecane-2-one.

Doctors and patients continue to need improved testosterone gel products having good stability, cosmetic properties, and efficacy, especially such products that also benefit from cost advantages or improved performance relative to current available product options.

SUMMARY

The following description relates to pharmaceutical compositions, such as compositions in the form of a gel ("gel compositions"), that include an active pharmaceutical ingredient ("active ingredient") that can be applied to the skin to transdermally administer the active ingredient to a patient. The active ingredient can be any that is desired for transdermal administration, though gel compositions of the invention that include testosterone as the active ingredient have been found to exhibit particularly useful or advantageous properties compared to other testosterone gel compositions currently marketed.

Examples of gel compositions as described can include a combination of ingredients that includes a solvent, cosolvent, polyol, gel-forming polymer (i.e., "thickener"), and optional pH adjusting ingredient (PH-modifier), to provide bioavailability of the active ingredient that is as good as, equivalent to, or better than certain currently-available commercial products such as Testim®, testosterone gel and Androgel® testosterone gel. Advantageously, the gel compositions described herein can achieve useful, desirable, or improved functional and cosmetic properties without the need for certain complicated (also potentially expensive) or cosmetically undesirable (e.g., due to odor) ingredients present in one or more of those commercial products. The ingredients used in the presently described gel compositions (solvent, cosolvent, polyol, polymer, and pH-modifier) are relatively simple and inexpensive, well known, and widely available.

Advantageously, the pharmaceutical compositions as described do not require and can preferably exclude a "Hsieh enhancer" such as oxacyclohexadecane-2-one as described in U.S. Pat. Nos. 7,320,968 and 5,023,252 (The entirety of these two patent documents, and other patent documents legally related thereto based on a common priority, are incorporated herein by reference). Pharmaceutical compositions of the present description can exclude the presence of any one or more of these "Hsieh enhancers" described in U.S. Pat. No. 7,320,968 (and its family members) or U.S. Pat. No. 5,023,252. Such enhancers are said to be lipophilic, and certain specific Hsieh enhancers are said to be "macrocyclic" meaning a cyclic compound having at least 12 carbon atoms in the cyclic ring. Examples of macrocyclic enhancers include: (A) macrocyclic ketones, for example, 3-methylcyclopentadercanone (muscone), 9-cycloheptadecen-1-one (civetone), cyclohexadecanone, and cyclopentadecanone (normuscone); and (B) macrocyclic esters, for example, pentadecalactones such as oxacyclohexadecan-2-one (cycloperitadecanolide; omega-pentadecalactone).

As another example, the commercially available AndroGel® testosterone gel composition includes isopropyl myristate as an enhancer. The presently-described pharmaceutical compositions do not require and can optionally exclude isopropyl myristate.

A testosterone gel composition as described herein, having useful or advantageous performance, does not require and specifically excludes any significant amount of a "Hseih enhance" and/or any significant amount of a isopropyl myristate. A testosterone gel composition as described herein may be prepared with ingredients that are generally available commercially, and by relatively simple manufacturing steps and methods. Embodiments of the resultant gel composition do not exhibit an undesired odor that can arise from the presence of a "Hseih enhancer."

Data show that testosterone gel compositions described herein can exhibit transdermal absorption of testosterone that is as good as, e.g., equivalent to, or better than absorption of testosterone associated with commercial products such as the Testim® testosterone gel and Androgel® testosterone gel products. The testosterone gel compositions can also be stable, and can have desirable cosmetic, tactile properties (e.g., texture), rheological properties including diminished, and reduced or suppressed undesirable odor, preferably an absence of any noticeable undesirable odor.

In one aspect, the invention relates to a pharmaceutical composition that contains: about 0.5 to about 10 weight percent testosterone; solvent comprising ethyl alcohol; cosolvent system comprising a cosolvent selected from diisopropyl adipate, methyl laurate, oleyl alcohol, and combinations thereof; polyol system comprising a polyol selected from glycerine, propylene glycol, polyethylene glycol, and combinations thereof; and gel-forming polymer, wherein the weight percent is based on total weight of the pharmaceutical composition.

In another aspect the invention relates to a pharmaceutical composition in the form of a gel, consisting essentially of: about 0.5 to about 10 weight percent testosterone; ethyl alcohol; diisopropyl adipate; methyl laurate; oleyl alcohol; glycerine; propylene glycol; polyethylene glycol polyol; gel-forming polymer; purified water; and optional pH-modifier, wherein the weight is based on total weight of the pharmaceutical composition.

In another aspect, the invention relates to a pharmaceutical composition in the form of a gel, consisting of: about 0.5 to about 10 weight percent testosterone; ethyl alcohol; cosolvent system consisting of diisopropyl adipate, methyl laurate, and oleyl alcohol; polyol system consisting of glycerine, propylene glycol, polyethylene glycol; gel-forming polymer; purified water; and optional pH-adjuster, wherein the weight percent is based on total weight of the pharmaceutical composition.

In yet another aspect, the invention relates to a package containing from 3 to 6 grams pharmaceutical composition. The composition contains: about 0.5 to about 10 weight percent testosterone; solvent comprising ethyl alcohol; cosolvent system comprising cosolvent selected from diisopropyl adipate, methyl laurate, oleyl alcohol, and combinations thereof; polyol system comprising polyol selected from glycerine, propylene glycol, polyethylene glycol, and combinations thereof; and gel-forming polymer, wherein the weight percent is based on total weight of the pharmaceutical composition.

In another aspect, the invention relates to a method for treating a condition associated with a deficiency of endogenous testosterone in a male patient. The method includes administering to the patient a pharmaceutical composition that contains: about 0.5 to about 10 weight percent testosterone; solvent comprising ethyl alcohol; cosolvent system comprising cosolvent selected from diisopropyl adipate, methyl laurate, olcyl alcohol, and combinations thereof; polyol system comprising polyol selected from glycerine, propylene glycol, polyethylene glycol, and combinations thereof; and gel-forming polymer, wherein the weight percent is based on total weight of the pharmaceutical composition.

In yet another aspect the invention relates to a method for transdermal delivery of testosterone to a patient. The method includes administering to the patient a pharmaceutical composition in the form of a gel, which contains: about 0.5 to about 10 weight percent testosterone; solvent comprising ethyl alcohol; cosolvent system comprising cosolvent selected from diisopropyl adipate, methyl laurate, oleyl alcohol, and combinations thereof; polyol system comprising polyol selected from glycerine, propylene glycol, polyethylene glycol, and combinations thereof; and gel-forming polymer, wherein the weight percent is based on total weight of the pharmaceutical composition.

In yet another aspect the invention relates to a method for treating hypogonadism in a patient. The method includes administering to the patient a pharmaceutical composition in the form of a gel, which contains: about 0.5 to about 10 weight percent testosterone; solvent comprising ethyl alcohol; cosolvent system comprising cosolvent selected from diisopropyl adipate, methyl laurate, oleyl alcohol, and combinations thereof; polyol system comprising polyol selected from glycerine, propylene glycol, polyethylene glycol, and combinations thereof; and gel-forming polymer, wherein the weight percent is based on total weight of the pharmaceutical composition.

In yet another aspect the invention relates to a method for maintaining an effective concentration of testosterone in the blood serum of a male for treating hypogonadism. The method includes transdermally delivering to the male by applying to the skin a pharmaceutical composition in the form of a gel. The gel contains: about 0.5 to about 10 weight percent testosterone based on total weight of the pharmaceutical composition; solvent comprising ethyl alcohol; cosolvent system comprising a cosolvent selected from diisopropyl adipate, methyl laurate, oleyl alcohol, and combinations thereof; polyol system comprising a polyol selected from glycerine, propylene glycol, polyethylene glycol, and combinations thereof; and gel-forming polymer. The pharmaceutical composition is applied to skin of the male in the form of a unit dose that contains about 25 mg to about 200 mg of testosterone and is maintained on the skin for a period of time sufficient for delivery of the testosterone to the male's systemic circulation such that, following a single application of the unit dose to the skin, the amount of circulating testosterone ($AUC_{0-24}$) in blood serum of the male achieved in a 24-hour period following the application is about 1,000 to about 350,000 pg·h/mL (picogram-hour/milliliter) greater than the amount of circulating testosterone ($AUC_{0-24}$) in the blood serum of the male that would have been achieved in the same 24-hour period had the dose not been administered.

DETAILED DESCRIPTION

While the present invention may be embodied in many different forms, the following description includes certain specific testosterone gel composition embodiments that particularly relate to treating hormone deficiency or hypogonadism in males. The present description is not to be limited to these exemplary embodiments.

The following description relates to pharmaceutical compositions that may take the form of a gel (or "hydroalcoholic gel") composition useful for transdermal administration of an active pharmaceutical ingredient, for example testosterone. This description explains that the pharmaceutical composition may preferably take the form of a pharmaceutical gel composition. But while a gel composition may be an exemplary or preferred form of a described pharmaceutical composition, other various forms of transdermal pharmaceutical compositions described herein can also be useful, including creams, dispersions, emulsions, lotions, ointments, thickened solutions, etc.

The pharmaceutical composition contains the active ingredient such as testosterone in an amount and form effective to treat a condition of a patient. The pharmaceutical composition additionally contains various inactive (not pharmaceutically active) ingredients that in combination can produce a combination of desired properties including viscosity and other rheological properties, desired tactile (e.g., feel and texture) properties, desirable (e.g., non-offensive) odor properties, and useful or advantageous properties of effectively allowing transdermal passage of the active ingredient to the blood stream of a patient.

Exemplary pharmaceutical compositions as described herein can be in the form of a gel that includes: an active ingredient that can be an androgen suitable for transdermal administration, such as testosterone; solvent that includes a straight or branched lower alcohol (e.g., a $C_2$, $C_3$, or $C_4$ alcohol) such as ethyl alcohol (ethanol) or isopropyl alcohol (isopropanol) or a combination of two or more such lower alcohols; cosolvent or a combination of cosolvents (a single cosolvent or combination of two or more cosolvents being referred to as a "cosolvent system") that can include one or more of diisopropyl adipate, methyl laurate, and a $C_{14}$ to $C_{22}$ alcohol (e.g., oleyl alcohol); polyol or a combination of polyols (a single polyol or combination of two or more polyols being referred to as a "polyol system") that can include one or more of glycerine, propylene glycol, and polyethylene glycol; a gel-forming or "gelling" polymer (a.k.a., a "thickener") that affects viscosity of the pharmaceutical composition; and an optional pH-modifier such as a base in an amount to desirably affect pH of the pharmaceutical composition.

The active ingredient can be an androgen such as testosterone, including any suitable form of testosterone such as 17-β-hydroxyandrost-4-en-3-one. The amount of active pharmaceutical ingredient (e.g., testosterone) in a gel composition can be an amount to produce a desired dosage upon application of the gel composition to a patient in need thereof and to be treated, for example an amount in the range from 0.25 to 10 percent by weight testosterone (e.g., 17-β-hydroxyandrost-4-en-3-one), e.g., from 0.5 to 5 or from 0.5 to 2 percent by weight testosterone (e.g., 17-β-hydroxyandrost-4-en-3-one), based on a total weight of the pharmaceutical composition. A concentration of testosterone that has been used for commercial testosterone gel compositions is about 1 percent by weight based on total weight of the testosterone gel composition.

In addition to the active ingredient, the described pharmaceutical compositions (e.g., gels) include inactive ingredients to provide functional (e.g., rheological and absorption) properties, tactile properties, and cosmetic (e.g., odor, texture) properties. These inactive ingredients can include one or more solvent, cosolvent, gelling polymer, water, and optional base or other pH-adjusting or pH-modifying material. Additionally, the described pharmaceutical compositions may optionally include other minor ingredients or excipients such as a stabilizer, emollient, antimicrobial, fragrance, and the like, in a low amount such as below 1 percent, below about 0.5 percent, or below about 0.2 percent by weight based on total weight pharmaceutical composition.

Examples of useful solvents include lower alcohols capable of containing the active pharmaceutical ingredient in a dissolved form. Lower alcohols include saturated alkyl (straight or branched) alcohols having four or fewer (e.g., 2, 3, or 4) carbon atoms, with particular examples including ethanol and isopropanol. A lower alcohol such as ethyl alcohol can be used as the solvent for testosterone as an active pharmaceutical ingredient. Testosterone is relatively soluble in ethyl alcohol, having a reported solubility of 0.17 grams per gram ethyl alcohol. A pharmaceutical gel composition can include any desired and useful amount of solvent (e.g., lower alcohol such as ethyl alcohol), with amounts in the range from 70 to 90 weight percent and from 75 to 85 weight percent (e.g., about 77 or about 78 weight percent, such as 78.35 weight percent) ethyl alcohol being preferred for certain pharmaceutical gel compositions described herein that contain testosterone.

One or more additional solvent (e.g., "cosolvent") can also be included in the pharmaceutical gel composition in combination with the active ingredient and lower alcohol (primary) solvent described above. According to preferred pharmaceutical gel compositions, a certain specific combination of cosolvents has been identified to provide desired or advantageous properties for a testosterone gel composition, the combination including diisopropyl adipate, methyl laurate, and an alkyl (branched, straight, unsaturated, or saturated) alcohol having from 14 to 22 carbon atoms such as oleyl alcohol. Extensive experimentation led to the unexpected discovery that testosterone gel compositions containing this combination of cosolvents, in combination with ethyl alcohol as the primary solvent, exhibit desired, effective (e.g., bioequivalence with currently marketed products) and/or advantageous skin penetration properties. These same gel compositions did not exhibit an undue or undesirable odor and did exhibit useful or advantageous rheological and tactile properties. Extensive experimentation also identified useful and preferred amounts of total cosolvent useful amounts of the three cosolvents taken in total), and useful amounts of each of the three cosolvents (individually, and relative to each other) for use as a cosolvent system in a gel composition.

A total amount of the combination of three cosolvents in a preferred cosolvent system (diisopropyl adipate, methyl laurate, and oleyl alcohol) in a testosterone gel composition, can be any useful amount, with an exemplary range being from 1 to 12 weight percent of these three ingredients, in total, based on the total weight of the composition, more preferably from about 2 to about 10 weight percent, or from about 2 to about 8 weight percent, based on a total weight of the composition.

Within these ranges, amounts of each of the three cosolvents of the preferred cosolvent system can be selected as desired, and preferably as follows. Preferred amounts of diisopropyl adipate can be in the range from 0.5 to 5 weight percent, e.g., from about 1 to about 3.5 weight percent or from 1 to 2 weight percent based on total weight pharmaceutical composition. Preferred amounts of methyl laurate can be in the range from 0.1 to 3 weight percent, e.g., from about 0.2 to about 2.5 weight percent, or from 0.2 to 0.4 weight percent based on total weight pharmaceutical composition. Preferred amounts of $C_{14}$ to $C_{22}$ (e.g., oleyl) alcohol can be in the range from 0.5 to 5 weight percent, e.g., from about 1 to about 3.5 weight percent, or from 1 to 2 weight percent based on total weight pharmaceutical composition.

Relative amounts (by weight) of diisopropyl adipate to $C_{14}$ to $C_{22}$ (e.g., oleyl) alcohol can be about 1 to 1, more generally within a range from 0.8 to 1.2 grams diisopropyl adipate per gram $C_{14}$ to $C_{22}$ (e.g., oleyl) alcohol. A preferred amount (by weight) of methyl laurate relative to diisopropyl adipate (or, alternately, relative to the $C_{14}$ to $C_{22}$ (e.g., oleyl) alcohol) can be an amount of methyl laurate (by weight) that is less than the amount of diisopropyl adipate (alternately $C_{14}$ to $C_{22}$ (e.g., oleyl) alcohol), e.g., amount that is in a range from about 10 percent (by weight) to about 70 percent (by weight) of the amount of diisopropyl adipate (alternately $C_{14}$ to $C_{22}$ (e.g., oleyl) alcohol). Relative amounts (by weight) of diisopropyl adipate to $C_{14}$ to $C_{22}$ (e.g., oleyl) alcohol to methyl laurate can be (0.8-1.2):1:(0.1-0.7).

One particular cosolvent system of a pharmaceutical composition may contain about 1.5 weight percent diisopropyl adipate, about 0.25 weight percent methyl laurate, and about 1.5 weight percent oleyl alcohol, based on total weight pharmaceutical composition. Another particular cosolvent system of a pharmaceutical composition may contain a ratio of about 6:1:6 diisopropyl adipate to methyl laurate to oleyl alcohol.

Preferred pharmaceutical gel compositions also include one or a combination of two or more polyols (a polyol system) to provide desired or advantageous tactile properties in combination with desired functional properties. Examples of useful polyols include one or a combination of propylene glycol, polyethylene glycol (e.g. polyethylene glycol 1000; the "1000" stands for an approximate or average molecular weight of the polyethylene glycol), and glycerine. These three polyols, in combination, have been found to impart positive tactile attributes to a pharmaceutical gel composition as described. The use of one or more of these polyols at a reasonable level can impart a smooth, slippery skin feel when the gel composition is applied, as opposed to a sticky or tacky feel.

Based on extensive experimentation, pharmaceutical gel compositions that include testosterone as an active pharmaceutical ingredient, ethanol solvent, and a polyol system that includes a combination of propylene glycol, polyethylene glycol (e.g. polyethylene glycol 1000), and glycerine, can exhibit desired, effective, or advantageous functionality. These gel compositions have been determined to not exhibit undue or undesirable odor, while exhibiting useful or advantageous rheological, tactile, and cosmetic properties. Extensive experimentation also identified useful and preferred amounts of total amounts of polyol (i.e., useful amounts of the three polyols taken in total), and useful amounts of each polyol (individually, and relative to each other) in a gel composition.

Polyols, including the described combination of polyols in the described amounts and relative amounts, can also contribute to stability of a testosterone gel composition, by providing a reduced freezing point and resistance to freezing, and resistance to testosterone degradation due to temperature cycling or freeze-thaw cycling.

A total amount of a polyol system containing the three identified polyols—propylene glycol, polyethylene glycol (e.g. polyethylene glycol 1000), and glycerine—in a testosterone gel composition, can be any useful amount, with an exemplary range being from 5 to 15 weight percent of these three polyols, in total, based on the total weight of the pharmaceutical gel composition, more preferably from 7 to 14 weight percent or from 8 to 12 weight percent.

Within these ranges, amounts of each polyol can be selected as desired, for example as follows. Preferred amounts of propylene glycol can be in the range from 2 to 8 weight percent, e.g., from about 3 to about 7 weight percent. Preferred amounts of polyethylene glycol can be in the range from 0.2 to 0.8 weight percent, e.g., from about 0.3 to about 0.7 weight percent. Preferred amounts of glycerine can be in the range from 2 to 8 weight percent, e.g., from about 3 to about 7 weight percent. Relative amounts (by weight) of propylene glycol to glycerine can be about 1 to 1, more generally within a range from 0.8 to 1.2 grams propylene glycol to glycerine. A preferred amount (by weight) of polyethylene glycol relative to propylene glycol (or, alternately, relative to the glycerine) can be an amount of polyethylene glycol (by weight) that is less than fifty percent of the amount (by weight) of propylene glycol (alternately glycerine), e.g., an amount that is in the range from about 5 percent (by weight) to about 25 percent (by weight) polyethylene glycol to propylene glycol (alternately glycerine).

One particular polyol system of a pharmaceutical composition may contain about 0.5 weight percent polyethylene glycol (e.g., PEG 1000), about 5.0 weight percent propylene glycol, and about 5.0 weight percent glycerine, based on total weight pharmaceutical composition.

The described pharmaceutical compositions also include a gel-forming polymer or "thickener" for use in increasing the viscosity of the composition. Increased viscosity retards the flow of the composition, thus allowing for improved surface cling. Increased viscosity retards also the movement of particles dispersed in the composition, allowing for compounds dispersed therein to remain suspended therein for relatively long periods of time. A pharmaceutical gel composition as described herein may have any desired or useful viscosity. Examples of gel-forming polymers include various natural and synthetic polymeric materials known in the pharmaceutical composition and dosage form arts for increasing viscosity of a pharmaceutical composition or dosage form, including: cellulosic polymers, for example, cellulose, hydroxyethylcellulose, carboxymethylcellulose, and hydroxypropylmethylcellulose; polyalkylene oxide polymers (e.g., polyethylene oxide), polyvinyl alcohol, and acrylic polymers (e.g., acrylic acid co-polymers and homopolymers).

In certain pharmaceutical composition embodiments, preferred gel-forming polymers can be carbomer polymers, for example non-linear polymers of acrylic acid cross-linked with a polyalkenyl polyether. Examples of carbomers useful in pharmaceutical compositions as described include carboxypolymethylene, carboxyvinyl polymer, and alkyl acrylates, for example, acrylic acid-alkyl methacrylate copolymers. Examples also include polymers of acrylic acid cross-linked with polyalkenyl ethers or divinyl glycol such as those that make up the Carbopol® line of polymeric thickeners (e.g., Carbopol® 980, Carbopol® 980 NF, Pemulen™ TR-1 (acrylic acid-alkyl methacrylate copolymer) polymers) and similar polymeric thickeners.

These and other useful gel-forming polymers can be a homopolymer or copolymer having a polymeric backbone made up of polymerized acrylic acid monomers, which may become crosslinked. Exemplary such polyacrylate gel-forming polymers contain long polymer chains having pendant carboxylic acid functionalities, crosslinked, e.g., with polyalkenyl polyethers.

Certain presently preferred testosterone gel compositions of the present description include a gel-forming polymer as described. Examples of preferred amounts of carbomer gel-forming polymer (e.g., polyacrylate) in a gel composition can be useful to achieve desired viscosity and other functional and cosmetic properties, with amounts in the range from 0.1 to 10 percent by weight (based on the total weight of the pharmaceutical gel composition) being useful, and preferred amounts being in the range from 0.2 to 6 or from 0.3 to 3 weight percent based on total weight pharmaceutical composition.

In pharmaceutical compositions that contain acidic materials, e.g., an acidic gel-forming polymer such as a carbomer, a pH-modifier may be included. A pH-modifier can be a basic ingredient that affects pH such as by neutralizing an acidic component of the gel composition. In particular, certain of the preferred gel composition described herein can include gel-forming polymer that includes pendant acidic (carboxylic acid) groups and a pH-modifier (base) to neutralize such pendant acid groups and impart a desired pH (or "apparent pH") to the gel.

The type of base useful in a gel composition can be any base useful to affect pH as desired, such as to neutralize acid functionalities of a polyacrylate gel-forming polymer, and that also is not incompatible with the gel composition generally. Examples of useful bases include sodium hydroxide (e.g., 0.1 normal (N) sodium hydroxide), tromethamine, and others. A preferred base for certain pharmaceutical gel compositions may be tromethamine. The amount of base included in pharmaceutical gel composition can be any desired amount, such as an amount sufficient to affect pH as desired, such as to neutralize acid functionalities of a polyacrylate gel-forming polymer.

In selecting a combination of base chemistry and concentration, these may preferably be selected to result in a gel composition that is physically stable and clear (not cloudy). For example, when 4.75% of 0.1N sodium hydroxide was used in a system with ethanol as solvent, a resulting sodium salt precipitated in the ethanol system, evident as cloudiness. Gel compositions using tromethamine remained clear and colorless white maintaining a consistent viscosity and stability.

A base may be added to a pharmaceutical composition to provide a desired pH reading using a standard pH meter. As used herein, the term "apparent pH" refers a result of a measurement made using a standard pH meter by placing the electrode into a pharmaceutical gel composition as described, as if to measure pH of the pharmaceutical gel composition. The pH meter can be any standard pH meter, and the measurement can be performed at standard conditions of testing for pH of an aqueous liquid. A pharmaceutical composition as described herein may include some amount of water, but may sometimes include a relatively low amount of water and a high amount of non-water solvent and cosolvent, along with other non-water ingredients such as polyol, gelling polymer, and solids. As a consequence, a value obtained by taking a measurement of a pharmaceutical gel composition as described using a pH meter, may not necessarily be a measure of a concentration of hydrogen ions in the composition. Still, a standard pH meter is capable of taking a measured reading from the composition when the electrode is placed in the pharmaceutical composition as if taking a pH measurement. If the reading of the pH meter is not considered a true pH of the pharmaceutical composition, due to its relatively low water content, the measurement is still considered to be an "apparent pH" of the pharmaceutical composition for purposes of the present description and claims.

According to certain examples of pharmaceutical gel composition as described, an apparent pH of these compositions may be in a range from 4.5 to 6.5, e.g., from 5.5 to 6.5. Still, compositions having an apparent pH outside of these identified ranges may still be useful pharmaceutical compositions.

According to certain particularly preferred testosterone gel compositions, combinations of certain preferred ingredients can be included in amounts also described, to provide preferred properties such as preferred skin penetration properties, preferred viscosity, and preferred tactile properties. The ingredients of the particularly preferred pharmaceutical gel compositions include the lower alcohol solvent ethanol; a cosolvent system (including diisopropyl adipate, methyl laurate, and oleyl alcohol); and a polyol system (including propylene glycol, polyethylene glycol, and glycerine) each in amounts as described herein. Exemplary gel compositions can also contain these ingredients along with an active pharmaceutical ingredient, gel-forming polymer, optional pH-modifier, and water, in the absence or substantial absence of other ingredients. Such compositions are considered to consist of or consist essentially of these ingredients. A substantial absence of other ingredients can allow for a small amount of such other ingredients, e.g., less than 1, 0.5, or 0.2 weight percent of other added ingredients based on a total weight of the pharmaceutical composition.

A pharmaceutical composition described as "consisting of" a group of specific ingredients is a composition made by combining the specified ingredients and no other identifiable ingredient. The pharmaceutical composition may include other (non-ingredient) materials only to the extent that the other materials were useful or appurtenant to preparation of one of the recited ingredients, such as the gel-forming polymer, solvent, cosolvent, polyol, active ingredient, or pH-modifier, and then only in a functionally insignificant amount.

A pharmaceutical composition described as "consisting essentially of" a group of specific ingredients is a composition made by combining the specified ingredients and no other identifiable ingredient other than optional minor (e.g., "excipient") ingredients such as a stabilizer, emollient, antimicrobial agent, coloring agent, fragrance, and the like, in a low amount, such as, by way of example, below about 1, 0.5 percent, or below about 0.2 percent by weight total such additional ingredients based on a total weight of the pharmaceutical composition.

The pharmaceutical composition of the present description may be formulated and prepared using conventional methods and equipment known in the pharmaceutical arts, such as by relatively simple combining, mixing, and stirring steps using known types of equipment. Standard glassware or stainless steel mixing vessels may be used. The composition can be formulated typically at mom temperature, e.g., at or around 25° C., or slightly above and at atmospheric pressures.

For purposes of a single example, a preferred pharmaceutical composition as described can be prepared by a method that includes steps useful to prepare known versions of alcohol gels, including combining ingredients in a manner to result in a stable and effective transdermal gel. Useful methods can include steps that ensure desired functionality of a gel-forming polymer, such as by an order of addition of ingredients that hydrates and optionally neutralizes a gel-forming carbomer polymer (if used). An example of a method useful to prepare a one-percent testosterone gel composition can include a step of hydrating gel-forming polymer or polymers (e.g., Carbopol® and Pemulen™ (acrylates) ingredients) in a portion of ethanol solvent. Testosterone, USP, is dissolved in a separate portion of ethanol. The gel-forming polymer is then combined with the ethanolic solution of testosterone.

With the exception of aqueous tromethamine as a pH-modifier, the remaining ingredients of the pharmaceutical composition can be added to this combined ethanolic mixture either in a single subsequent step of adding a mixture of the remaining ingredients, or in multiple steps of adding multiple ingredients singly. For example, a system of cosolvents may be added together in one step and one or more polyols of a polyol system may be added separately or together. A tromethamine solution can be added in a final step. All ingredients are miscible in ethanol. Thus, after each component addition the result remains a solution.

A pharmaceutical composition as described may be contained in a tube, a sachet, a metered pump, or another useful dispensing device. Such a tube or sachet may contain one unit dose of the composition, e.g., 5 grams of testosterone gel which can contain 50 mg of testosterone. A metered pump may be capable of dispensing one metered dose of the composition per actuation, which metered dose may or may not contain a unit dose.

As one example, a gel composition can be dispensed from a hand-held metered-dose pump capable of delivering a metered dose of the gel, such as about 1.25 grams (g) of the testosterone gel with each actuation, e.g., with four pump actuations, a total of 5 grams (a single unit dose) of the testosterone gel may be delivered. In another embodiment, the gel composition can be packaged in foil packet. For example, each packet can hold a single unit dose of the gel, such as an amount of about 5 grams of testosterone gel. A patient can tear the packet along a perforated edge to remove the gel. As another alternative, a gel composition as described can be dispensed from a rigid multi-dose container (e.g., with a hand pump) having a foil packet of the composition inside the container. Any useful dispensing option, as described or otherwise, can allow a user to deliver an accurate amount of a desired dosage of the gel composition, by mass or volume, (e.g., 5.0 g, 7.5 g, 10 g, etc).

A condition in a patient related to below-normal androgen concentration in blood serum of the patient may be treated by administering to the patient a pharmaceutical composition as described, such as a topically-delivered, transdermal gel composition as described. A pharmaceutical gel composition may be applied and rubbed onto skin of the patient, such as intact, clean, and dry skin of the shoulder, upper arm, axilla, the upper torso, or thigh, and maintained thereon for a period of time sufficient for delivery of androgen to the blood serum of the patient.

The dosage amount will depend upon the condition to be treated, the frequency of administration of the dose, and the amount of androgen in the gel composition. Without limitation, a pharmaceutical gel composition as described can be applied to skin of a patient in the form of a unit dose that contains from about 25 milligrams (mg) to about 200 mg of testosterone. A single unit dose of the testosterone gel composition can be in a range from 2.5 grams (which at a 1% concentration contains 25 mg of testosterone) to 20 grams (which at a 1% concentration contains 200 mg of testosterone). As particular examples, a single unit dose of the testosterone gel composition can be 5 grams (containing 50 mg of testosterone) or 10 grams (containing and 100 mg of testosterone).

For the purpose of treating male hypogonadism, a preferred once daily dosage amount (e.g., unit dose) of a gel composition of the present invention (containing 1 percent testosterone) can be from about 1 to about 10 grams of the gel composition, and preferably about 5 to about 10 grams of the gel composition. The unit dose can be maintained on the skin for a period of time sufficient for delivery of the testosterone to the patient's systemic circulation such that, following a single application of the unit dose to the skin, the amount of circulating testosterone ($AUC_{0-24}$) in blood serum of the patient achieved in a 24-hour period following the application is a useful or desired amount, such as an amount that is about 46,000 to about 95,000 pg·h/mL (picogram-hour/milliliter) (e.g., about 53,000 to about 82,800 pg·h/mL; about 50,000 to about 88,000 pg·h/mL, such as about 66,250 pg·h/mL) greater than the amount of circulating testosterone ($AUC_{0-24}$) in the blood serum of the patient that would have been achieved in the same 24-hour period had the dose not been administered.

In situations where a unit dose is applied, one or more of such unit doses may be administered to a patient, depending upon the condition to be treated, the amount of androgen to be delivered, and the frequency of administration. The number of such unit doses may be increased or decreased as needed, depending upon, as stated above, whether a desired clinical effect has been achieved and the concentration of androgen in the blood serum of the patient treated.

If, after a period of time has passed following the initial administration of a testosterone gel composition (for example, about 14 days), a desired clinical response has not been achieved or if the androgen concentration in the blood serum of the patient is determined and found to remain below the normal adult concentration thereof, i.e., below about 250 to about 300 ng·h/dL (nanogram-hour per deciliter) (i.e., 2,500 to about 3,000 pg·h/mL), the amount of the dose, the frequency of the dose, and/or the number of applications of the dose may be increased. Similarly, if, after a period of time has passed following the initial administration of the gel composition (for example, about 14 days), the androgen concentration in the blood serum of the patient is determined and found to be above the normal adult concentration thereof, the amount of the dose, the frequency of the dose, and/or the number of applications of the dose may be decreased.

Example 1

Gel compositions that can be used as a topical gel for delivery of testosterone, including certain pharmaceutical compositions of the invention, were prepared according to the following Tables. The ingredients and amounts of ingredients used in each example are given in percent by weight relative to the total weight of the composition.

TABLE 1

Testosterone Gel 1% Formulations (Example 1-1 through 1-11)

| Ingredient | Example | | | | | | | | | | |
| --- | --- | --- | --- | --- | --- | --- | --- | --- | --- | --- | --- |
| | 1-1 | 1-2 | 1-3 | 1-4 | 1-5 | 1-6 | 1-7 | 1-8 | 1-9 | 1-10 | 1-11 |
| Testosterone, USP | 1.0 | 1.0 | 1.0 | 1.0 | 1.0 | 1.0 | 1.0 | 1.0 | 1.0 | 1.0 | 1.0 |
| Ethyl alcohol, anhydrous, USP | q.s. to 100 | q.s. to 100 | q.s. to 100 | q.s. to 100 | q.s. to 100 | q.s. to 100 | 67.0 | 67.5 | 67.0 | 67.0 | q.s. to 100 |
| Glycerin, 99.7%, USP | 5.0 | 5.0 | 5.0 | 5.0 | 5.0 | 5.0 | — | — | — | — | 5.0 |
| Carbomer 980 | 1.5 | 1.5 | 1.5 | 1.5 | 1.5 | 1.5 | 0.9 | 0.9 | 0.9 | 0.9 | 1.5 |
| Pemulen ™ TR-1 | 0.3 | 0.3 | 0.3 | 0.3 | 0.3 | 0.3 | — | — | — | — | 0.3 |
| PEG 1000, NF | 0.5 | 0.5 | 0.5 | 0.5 | 0.5 | 0.5 | — | — | — | — | 0.5 |
| Tromethamine, | 0.1 | 0.1 | 0.1 | 0.1 | 0.1 | 0.1 | | | | | 0.1 |

TABLE 1-continued

Testosterone Gel 1% Formulations (Example 1-1 through 1-11)

| Ingredient | 1-1 | 1-2 | 1-3 | 1-4 | 1-5 | 1-6 | 1-7 | 1-8 | 1-9 | 1-10 | 1-11 |
|---|---|---|---|---|---|---|---|---|---|---|---|
| USP | | | | | | | | | | | |
| Sodium hydroxide (0.1N) | — | — | — | — | — | — | 4.72 | 4.72 | 4.72 | 4.72 | — |
| Propylene Glycol, USP | 5.0 | 5.0 | 5.0 | 13.0 | 5.0 | 6.0 | — | — | 8.0 | — | 8.0 |
| Pentadecalactone | 8.0 | — | — | — | — | — | — | — | — | — | — |
| dl-limonene | — | — | — | — | — | 2.0 | — | — | — | — | — |
| Diisopropyl adipate | — | — | — | — | 3.0 | — | — | — | — | — | — |
| Lauryl alcohol | — | — | — | — | — | 3.0 | — | — | — | — | 2.0 |
| Methyl laurate | — | — | — | — | 2.0 | 2.0 | — | — | — | — | 1.0 |
| Isopropyl myristate | — | 8.0 | — | — | — | — | 0.5 | — | — | — | — |
| Oleyl alcohol | — | — | — | — | 3.0 | — | — | — | — | 3.0 | — |
| Propylene glycol dicaprylate/dicaprate (Miglyol 840) | — | — | — | — | — | — | — | — | — | 3.0 | — |
| PG-dipelargonate | — | — | — | — | — | — | — | — | — | 0.6 | — |
| Purified Water, USP | 5.0 | 5.0 | 13.0 | 5.0 | 5.0 | 5.0 | q.s. to 100 | q.s. to 100 | q.s. to 100 | q.s. to 100 | 5.0 |
| Apparent pH | 5.3 | 5.2 | 5.2 | 5.4 | 5.5 | 5.0 | 5.1 | 5.4 | 5.5 | 5.3 | 5.7 |
| Viscosity, cP at 25° C. | 978 | 763 | 1,383 | 1,531 | 1,017 | 732 | 275 | 494 | 1,102 | 766 | 1,436 |
| Visual appearance | Clear | Clear | Clear | Clear | NA | NA | Clear | Clear | Clear | NA | Clear |

Based on the in vitro performance results of the Examples of Table 1, Example 1-5 had desired performance. Additional examples (1-5A, 1-5B, 1-5C, and 1-5D) were prepared having formulations similar to but different from the Example 5 formulation. The formulations of Examples 1-5A, 1-5B, 1-5C, and 1-5D varied in terms of the ratios and overall levels of cosolvents of the diisopropyl adipate, methyl laurate, oleyl alcohol cosolvent system. See Table 2 below.

TABLE 2

Testosterone Gel 1% Formulations (the "5-series")

| Ingredient | 1-5 | 1-5A | 1-5B | 1-5C | 1-5D |
|---|---|---|---|---|---|
| Testosterone, USP | 1.0 | 1.0 | 1.0 | 1.0 | 1.0 |
| Ethyl alcohol, anhydrous, USP | q.s. to 100 | 75.1 | q.s. to 100 | 77.3 | 78.3 |
| Glycerin, 99.7%, USP | 5.0 | 5.0 | 5.0 | 5.0 | 5.0 |
| Carbomer 980 | 1.5 | 1.5 | 1.5 | 1.5 | 1.5 |
| Acrylates (Pemulen TR-1) | 0.3 | 0.3 | 0.3 | 0.3 | 0.3 |
| PEG 1000, NF | 0.5 | 0.5 | 0.5 | 0.5 | 0.5 |
| Trometamine, USP | 0.1 | 0.1 | 0.1 | 0.1 | 0.1 |
| Propylene Glycol, USP | 5.0 | 5.0 | 5.0 | 5.0 | 5.0 |
| Diisopropyl adipate | 3.0 | 2.5 | 2.0 | 2.0 | 1.5 |
| Methyl laurate | 2.0 | 1.5 | 1.0 | 0.25 | 0.25 |
| Oleyl alcohol | 3.0 | 2.5 | 2.0 | 2.0 | 1.5 |
| Purified Water, USP | 5.0 | 5.0 | 5.0 | 5.0 | 5.0 |

Figure 2:
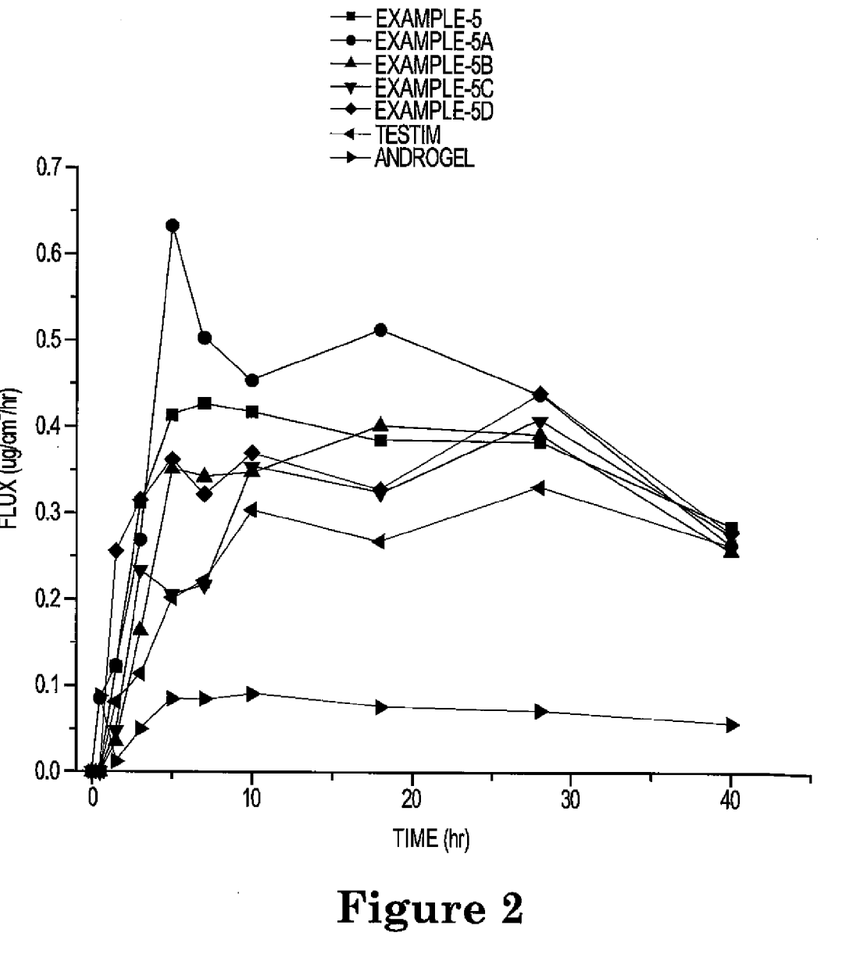
FIG. 2 is a graph showing flux of active ingredient of testosterone gel compositions, relative to time.

The performance of the "5-Series" Example formulations compared well to the commercial Testim® testosterone gel product. FIG. 2 illustrates performance data of the "5-series" compared to a Testim® testosterone gel product.

Example 2

In Vitro Evaluation of Percutaneous Absorption of Testosterone

Figure 1:
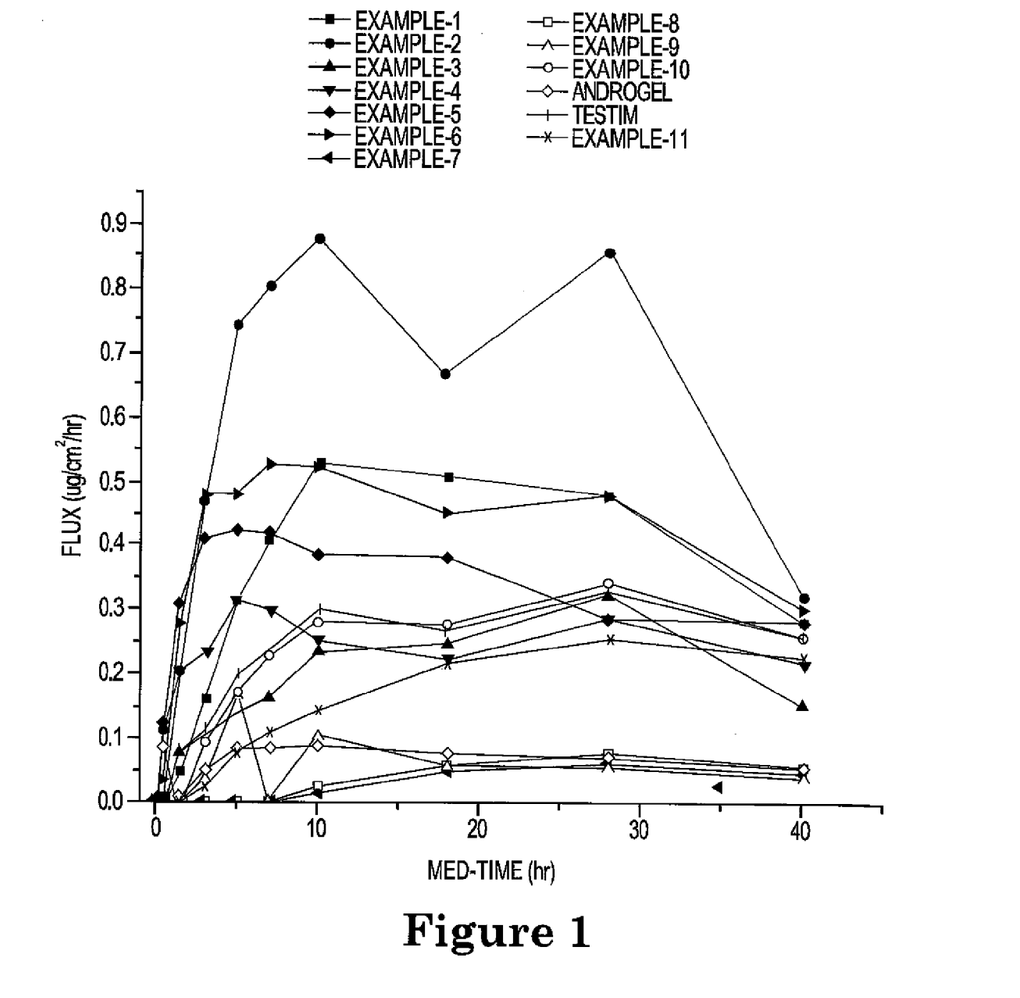
FIG. 1 is a graph showing flux of active ingredient of testosterone gel compositions, relative to time.

To characterize the percutaneous absorption pharmacokinetics of testosterone in the various Example formulations of Table 1 and Table 2, absorption was measured in human cadaver skin in vitro, using the finite dose technique and Franz diffusion cell (Franz, *J. Invest. Dermatol.* 65:190-195 (1975). Results are depicted at FIG. 1 and FIG. 2.

The example testosterone gel formulations described in Table 1 were initially screened in an in-vitro skin penetration study. The graph at FIG. 1 illustrates the results for in-vitro human skin penetration studies of Examples 1-through 1-11. The example testosterone gel formulations described in Table 2 were also tested in an in vitro skin penetration study. The graph at FIG. 2 illustrates the results for in vitro human skin penetration studies of Examples 1-5A-through 1-5D.

Example 3

The testosterone gel formulation shown in Table 3 is bioequivalent to Testim® testosterone gel, possesses good long term stability, can be manufactured with consistency, and is cosmetically pleasing to a patient, including a lack of undesirable odor.

TABLE 3

1% Testosterone Gel Formulation

| Component | Percent by weight |
|---|---|
| Ethyl alcohol, anhydrous, USP | 78.35 |
| Testosterone, USP | 1.00 |
| Glycerin, 99.7%, USP | 5.00 |
| Diisopropyl adipate | 1.50 |
| Methyl laurate | 0.25 |
| Oleyl alcohol, NF | 1.50 |
| Carbomer Homopolymer Type C*, NF (Carbomer 980) | 1.50 |
| Carbomer Copolymer Type B*, NF (Pemulen TR-1, Acrylates) | 0.30 |
| Propylene glycol, USP | 5.00 |

TABLE 3-continued

1% Testosterone Gel Formulation

| Component | Percent by weight |
|---|---|
| Polyethylene glycol 1000, USP | 0.50 |
| Purified Water, USP | 5.00 |
| Tromethamine, USP | 0.10 |

*(allyl pentaerythritol crosslinked)

The invention claimed is:

1. A pharmaceutical composition in the form of a gel, consisting essentially of:
   about 0.5 to about 10 weight percent testosterone;
   ethyl alcohol;
   diisopropyl adipate;
   methyl laurate;
   oleyl alcohol;
   glycerine;
   propylene glycol;
   polyethylene glycol polyol;
   gel-forming polymer;
   purified water; and
   optional pH-modifier, wherein the weight percent is based on total weight of the pharmaceutical composition.

2. A pharmaceutical composition according to claim 1 wherein the testosterone is present in a range from about 0.5 to about 2 weight percent.

3. A pharmaceutical composition according to claim 1 wherein the ethyl alcohol is present in a range from about 75 to about 85 weight percent.

4. A pharmaceutical composition according to claim 1 wherein a combination of the diisopropyl adipate, the methyl laurate and the oleyl alcohol is present in the composition in a range from about 1 to about 12 weight percent.

5. A pharmaceutical composition according to claim 1 wherein a combination of the glycerine, the propylene glycol and the polyethylene glycol polyol is present in the composition in a range from about 7 to about 14 weight percent.

6. A pharmaceutical composition according to claim 1 wherein the pH-modifier is tromethamine.

7. A pharmaceutical composition according to claim 1, wherein the gel-forming polymer is a carbomer polymer.

8. A pharmaceutical composition according to claim 1, consisting essentially of:
   1 weight percent testosterone;
   75 to 85 weight percent ethyl alcohol;
   1 to 2 weight percent diisopropyl adipate;
   0.2 to 0.4 weight percent methyl laurate;
   1 to 2 weight percent oleyl alcohol;
   3 to 7 weight percent glycerine;
   3 to 7 weight percent propylene glycol;
   0.3 to 0.7 weight percent polyethylene glycol;
   1 to 3 weight percent weight percent gel-forming polymer;
   purified water; and
   pH-modifier.

9. A pharmaceutical composition according to claim 1, consisting essentially of:
   about 1 weight percent testosterone;
   about 78 weight percent ethyl alcohol;
   about 1.5 weight percent diisopropyl adipate;
   about 0.25 weight percent methyl laurate;
   about 1.5 weight percent oleyl alcohol;
   about 5 weight percent glycerine,
   about 5 weight percent propylene glycol,
   about 0.5 weight percent polyethylene glycol;
   1.8 weight percent weight percent carbomer gel-forming polymer;
   about 4 weight percent purified water; and
   about 0.1 weight percent tromethamine.

10. A pharmaceutical composition according to claim 1 wherein the polyethylene glycol comprises polyethylene glycol 1000.

11. A pharmaceutical composition according to claim 1 wherein the pharmaceutical composition can be applied to skin of a patient in the form of a unit dose that contains about 25 mg to about 200 mg of testosterone, and maintained on the skin for a period of time sufficient for delivery of the testosterone to the patient's systemic circulation such that, following a single application of the unit dose to the skin, the amount of circulating testosterone ($AUC_{0-24}$) in blood serum of the patient achieved in a 24-hour period following the application is about 46,000 to about 95,000 pg·h/mL (picogram-hour/milliliter) greater than the amount of circulating testosterone ($AUC_{0-24}$) in the blood serum of the patient that would have been achieved in the same 24-hour period had the dose not been administered.

12. A package containing from 3 to 6 grams pharmaceutical composition according to claim 1.

13. A package containing from 3 to 6 grams pharmaceutical composition according to claim 1, wherein the package is adapted for dispensing a single dose of the pharmaceutical composition.

14. A package containing from 3 to 6 grams pharmaceutical composition according to claim 1, wherein the package is adapted for dispensing a metered volume of the pharmaceutical composition.

15. A package according to claim 14, wherein the package comprises multiple doses.

16. A package according to claim 12, wherein the package is a pump.

17. A pharmaceutical composition according to claim 1 wherein the diisopropyl adipate, methyl laurate and oleyl alcohol are present in the composition in a ratio from (0.8:1.2) to (0.1-0.7) to 1.

18. A method of treating a condition associated with a deficiency of endogenous testosterone in a male patient, the method comprising administering to the patient a pharmaceutical composition consisting essentially of:
   about 0.5 to about 10 weight percent testosterone;
   ethyl alcohol;
   diisopropyl adipate;
   methyl laurate;
   oleyl alcohol;
   glycerine;
   propylene glycol;
   polyethylene glycol polyol;
   gel-forming polymer;
   purified water; and
   optional pH-modifier, wherein the weight percent is based on total weight of the pharmaceutical composition.

19. The method of claim 18, wherein the pharmaceutical composition is administered to the patient's shoulder, upper arm, axilla, upper torso, thigh, or combination thereof.

20. A package comprising multiple doses of a pharmaceutical composition, the composition consisting essentially of:
   about 0.5 to about 2 weight percent testosterone;
   about 75 to about 85 weight percent ethyl alcohol;
   about 2 to about 10 weight percent cosolvent system, wherein the cosolvent system consists of diisopropyl adipate, methyl laurate, and oleyl alcohol;

about 7 to about 14 weight percent polyol system, wherein the polyol system consists of glycerine, propylene glycol, polyethylene glycol, and combinations thereof;
about 0.5 to about 3 weight percent carbomer gel forming polymer; and pH-modifier, wherein the weight percent is based upon the total weight of the pharmaceutical composition.

* * * * *